US005527276A

United States Patent [19]

Bruce

[11] Patent Number: 5,527,276
[45] Date of Patent: Jun. 18, 1996

[54] FLEXIBLE INFLOW/OUTFLOW CANNULA

[75] Inventor: Robert P. Bruce, San Jose, Calif.

[73] Assignee: Arthroscopic Assistants, Inc., San Jose, Calif.

[21] Appl. No.: 242,703

[22] Filed: May 13, 1994

Related U.S. Application Data

[63] Continuation of Ser. No. 3,427, Jan. 1, 1993, abandoned.

[51] Int. Cl.$^6$ .................................................. A61M 31/00
[52] U.S. Cl. .............................................. 604/54; 604/280
[58] Field of Search ............................ 604/54, 164, 264, 604/280; 433/91

[56] References Cited

U.S. PATENT DOCUMENTS

| | | |
|---|---|---|
| 4,596,563 | 6/1986 | Pande ........................................ 604/264 |
| 4,636,346 | 1/1987 | Gold et al. ............................... 264/139 |
| 4,688,554 | 8/1987 | Habib . |
| 4,799,495 | 1/1989 | Hawkins et al. . |
| 4,846,812 | 7/1989 | Walker et al. ........................... 604/264 |
| 4,865,593 | 9/1989 | Ogawa et al. ........................... 604/264 |
| 4,869,718 | 9/1989 | Brader ...................................... 604/164 |
| 4,878,894 | 11/1989 | Sutter et al. . |
| 4,926,860 | 5/1990 | Stice et al. . |
| 4,934,340 | 6/1990 | Ebling et al. . |
| 5,088,991 | 2/1992 | Weldon ..................................... 604/280 |
| 5,125,902 | 6/1992 | Berry et al. .............................. 604/164 |

OTHER PUBLICATIONS

*O'Connor's Textbook of Arthroscopic Surgery*, Heshmat Shahriaree–Editor, pp. 29 and 172, J. B. Lippincott Company (1984).
*Arthroscopic Surgery Principles & Practice*, Lanny L. Johnson, pp. 341–346, The C. V. Mosby Company (1986).
Product Data Sheet, "Ingress/Egress Cannulae," Richard Wolf Medical Instruments Corp., Rosemont, Ill.

*Primary Examiner*—Corrine M. McDermott
*Attorney, Agent, or Firm*—Donald J. Pagel, Jr.

[57] ABSTRACT

A flexible plastic cannula for use in directing liquid to or from the suprapatellar pouch during arthroscopic knee surgery. The cannula is comprised of a flexible elongated stem, a valve housing and an attachment means, all molded in a single piece of high density polyethylene. The stem is tapered along its length so that the end nearest the valve housing is relatively rigid, while the distal end is narrower and more flexible. The flexibility of the cannula stem is sufficient to allow it to bend with the knee during the arthroscopic surgery.

4 Claims, 2 Drawing Sheets

FLEXIBLE INFLOW/OUTFLOW CANNULA

This is a continuation of application Ser. No. 08/003,427, filed Jan. 1, 1993, now abandoned.

TECHNICAL FIELD

The present invention relates to a cannula for use in surgical procedures and more particularly to a flexible inflow/outflow cannula for use during arthroscopic surgery.

BACKGROUND ART

The basic techniques of arthroscopic surgery are thoroughly reviewed in medical textbooks such as O'Connor's Textbook of Arthroscopic Surgery, Heshmat Shahriaree—Editor, J. B. Lippincott Company (1984) [hereinafter referred to as O'Conner's]; and Arthroscopic Surgery Principles & Practice, Lanny L. Johnson, The C. V. Mosby Company (1986).

As is discussed in these references, arthroscopic surgery involves the insertion of a device, known as an arthroscope, into a joint region, such as the knee, elbow or shoulder, in order to allow the surgeon to view the internal condition of the joint.

In arthroscopic knee surgery, it is common practice to fill the suprapatellar pouch that surrounds the knee with a clear liquid, such as saline irrigation solution, in order to keep the field of view through the arthroscope clear. Since even a small amount of blood will cause the clear solution to become cloudy, means for draining and replenishing the irrigation solution are needed throughout the duration of the surgery.

This is typically accomplished by inserting a rigid inflow cannula into the suprapatellar pouch, above the patella, and attaching a tube between the inflow cannula and an elevated fluid reservoir. The arthroscope is inserted into the knee and a gravity or suction device is attached to one port of the arthroscope.

Fluid from the fluid reservoir is introduced into the suprapatellar pouch by opening an "on-off" valve on the inflow cannula. Fluid then enters the suprapatellar pouch under the force of gravity or mechanically induced pressure and is removed from the suprapatellar pouch by activating the suction or free flow gravity device attached to the arthroscope.

Alternatively, fluid can be introduced through the arthroscope and removed with a gravity device attached to the cannula (e.g. a flexible plastic tube running from the cannula to a bucket on the floor). In this method, the cannula is referred to as an outflow (or egress) cannula or as a drainage needle.

Typically, the cannulae that are used in arthroscopic knee surgery are rigid (unbending) cannulae. An example of a such a cannula is the rigid metal cannula shown in O'Conner's at page 29 (called a "drainage needle" because of its use in the second method discussed above). An example of a teflon outflow cannula is shown in O'Conner's at page 172.

During arthroscopic knee surgery, the surgeon typically rotates and bends the patient's knee, while the arthroscope and inflow/outflow cannula are positioned in the knee, in order to obtain a different view of the joint structure under examination.

This rotation and bending of the knee during the arthroscopic surgery can cause numerous problems with the rigid cannula. First, when the knee is bent, the flow of fluid through the rigid cannula is frequently completely blocked by the synovial lining of the suprapatellar pouch closing down on the end of the cannula. Second, when the knee is bent or rotated, a rigid cannula can bruise or puncture the suprapatellar pouch or other tissue.

SUMMARY OF THE PRESENT INVENTION

Briefly, the preferred embodiment of the present invention is an inflow/outflow cannula for use in arthroscopic knee surgery having a flexible stem that bends with the knee during the surgery. The cannula also includes a valve housing for accepting an "on-off" valve, and an attachment means for allowing equipment such as fluid lines to be attached to the cannula.

In the preferred embodiment, the flexible inflow/outflow cannula is comprised of a plastic material, such as high density polyethylene, and is injection molded so that the stem, valve housing and attachment means are all a single piece.

The flexible stem is tapered so that the widest end of the stem is relatively unbendable while the rest of the stem increases in flexibility as the narrowest end of the stem is approached. This tapering feature gives the cannula sufficient rigidity to allow it to be repositioned during surgery, while at the same time giving the cannula sufficient flexibility to bend with the knee as the surgeon rotates and bends the knee during the surgery.

DETAILED DESCRIPTION OF THE PREFERRED EMBODIMENT

Figure 1:
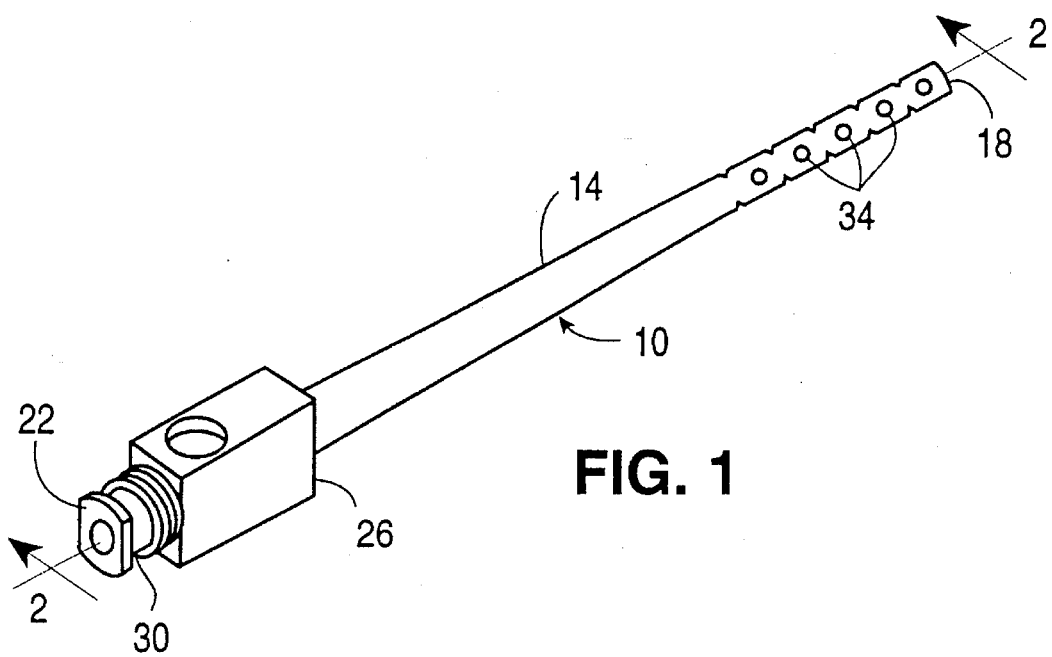
FIG. 1 is a perspective view of a flexible inflow/outflow cannula according to the present invention.

FIG. 1 is a perspective view of a flexible inflow/outflow cannula 10 for use in delivering liquids to or from body cavities during arthroscopic surgery. The cannula 10 comprises a stem 14, a distal end 18, a proximal end 22, a valve housing 26 and an attachment means 30. A plurality of apertures 34 are positioned near the distal end 18 of the stem 14.

Throughout this description, the term proximal is used to specify that an item under discussion is relatively closer to the proximal end 22 than to the distal end 18. Similarly, the term distal is used to specify that an item under discussion is relatively closer to the distal end 18 than to the proximal end 22.

Figure 2:
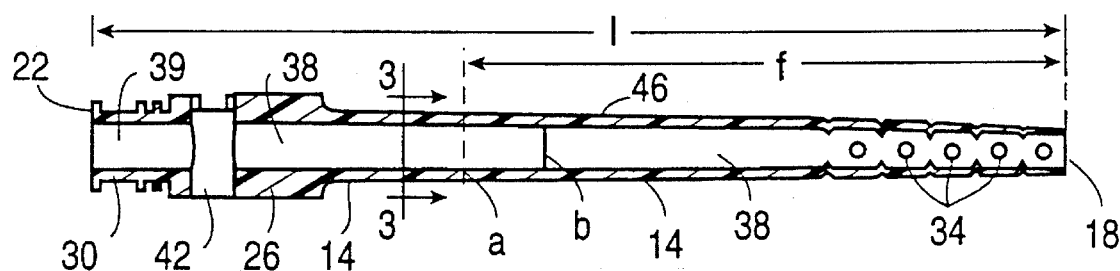
FIG. 2 is a cross-sectional view of the flexible cannula taken along the line 2—2 shown in FIG. 1.

FIG. 2 illustrates that the cannula 10 is a hollow device having a lumen 38 that extends from the distal end 18 through the stem 14, and into the valve housing 26. A lumen 39 extends from the proximal end 22, through the attachment means 30, and into the valve housing 26. The cannula 10 has a total length "l" of approximately four inches.

The lumens 39 and 38 are open at the proximal end 22 and distal end 18, respectively, to provide a means for liquid to enter and exit the cannula 10. Additionally, the apertures 34 extend through the stem 14 and into the lumen 38, thereby providing a plurality of passageways for fluid to flow into or out of the lumen 38.

In the preferred embodiment, the stem 14, valve housing 26 and attachment means 30 are injection molded from a polymeric material, such as high density polyethylene, to form a single piece instrument. The high density polyethylene sold by Dow Chemical Company under the designation Dow HDPE 25355N Resin (narrow molecular weight distribution copolymer) works quite well. Other materials compatible with use inside the human body and having the requisite flexibility properties could also be used to manufacture the cannula 10.

The valve housing 10 includes a vertical aperture 42 for accepting a valve 44 (shown in FIGS. 5 and 6) that controls the flow of fluid through the cannula 10 by providing a connection between the lumens 38 and 39.

The attachment means 30 is a connector, such as a LUER LOCK connector, which allows other pieces of equipment (e.g. fluid supply lines) to be attached to the cannula 10.

Figure 3:
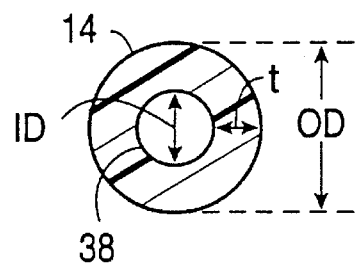
FIG. 3 is a cross-sectional view of the flexible cannula taken along the line 3—3 shown in FIG. 2.

The stem 14 is an elongated structure extending from the valve housing 26 to the distal end 18. FIG. 3 illustrates that a cross section of the stem 14 is circular in shape. The solid part of the stem 14 surrounds the lumen 38 and has an outside diameter (OD) which is the distance between a point on the outside surface of a cross-sectional slice of the solid part, to a co-planar point on the outside surface of the same cross-sectional slice 180 degrees away. Similarly, an inside diameter (ID) is defined as the distance between a point on the inside surface of a cross-sectional slice of the solid part, to a co-planar point on the inside surface of the same cross-sectional slice 180 degrees away. The solid part of the stem 14 has a thickness "t."

In the cannula 10, the stem 14 is tapered along its length, meaning that the outside diameter of the stem 14 is greater at the proximal end of the stem 14 than it is at the distal end 18, and decreases smoothly from the proximal end of stem 14 to the distal end 18. Similarly, the inside diameter of the stem 14 is greater at the proximal end than it is at the distal end 18 and decreases smoothly from proximal end to the distal end.

Stated differently, each proximal cross-sectional slice of the stem 14 has an outside diameter and an inside diameter that are greater than the outside diameter and inside diameter of an adjacent distal cross-sectional slice.

To further illustrate this point, a reference line "a" is shown in FIG. 2 located in the proximal end of the stem 14. A flexible segment 46 of the stem 14, extends from the reference line "a" to the distal end 18 and has a length "f" of approximately 2.5 inches (the reference line "a" marks the proximal end of the flexible segment 46. Also, reference line "a" illustrates a proximal cross-sectional slice of the stem 14, while a reference line "b" illustrates a distal cross-sectional slice). The outer diameter of the stem 14 at the reference line "a" is approximately 0.169 inches and the inner diameter at this line is approximately 0.119 inches. The outer diameter of the stem 14 at the distal end 18 is approximately 0.119 inches and the inner diameter at this point is approximately 0.090 inches.

Figure 4:
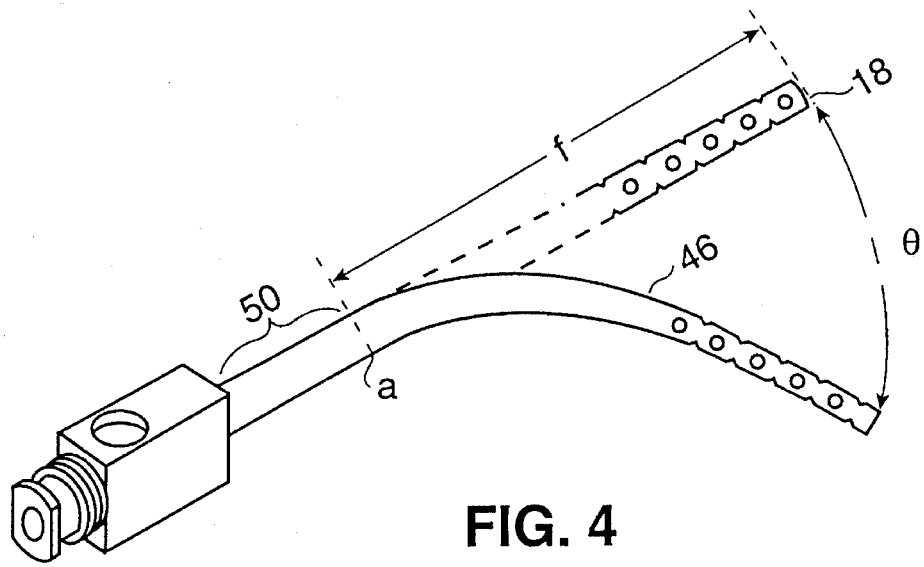
FIG. 4 is a perspective view illustrating the flexibility of the cannula shown in FIG. 1.

FIG. 4 illustrates that the flexible segment 46 has sufficient flexibility to bend through an angle θ. In the preferred embodiment the angle θ is approximately ninety degrees. The flexibility of the flexible segment 46 results from the "tapered" construction of the stem 14. Specifically, since the OD and ID of the stem 14 decrease smoothly, but at different rates between a reference line "a" and the distal end 18, the thickness of the stem 14 also decreases over this distance.

In the preferred embodiment, the thickness "t" of the stem 14 is about 0.025 inches at the reference line "a" and about 0.0145 inches at the distal end 18. This decrease in thickness of the stem 14 over the distance "f" results in the stem 14 becoming progressively more flexible as the distal end 18 is approached from the reference line "a." The increase in flexibility of the stem 14 on moving from the proximal end of stem 14 to the distal end 18 is referred to as "progressive flexibility."

When the distance "f" is about 2.5 inches, the reference line "a" marks the region of the stem 14 where the stem 14 begins to bend when a person grasps the proximal end 22 in one hand and applies downward force to the distal end 18, using the other hand, sufficient to cause the stem 14 to bend through an angle θ of approximately ninety degrees (force comparable to what would be exerted by the knee bending during arthroscopic surgery). Under these conditions, a rigid segment 50 of the stem 14 exists that has sufficient thickness "t" so that it does not bend to any significant extent relative to the flexible segment 46. When the downward force is removed, the stem 14 can be returned to its original "straight" position. Even when the stem 14 is bent to ninety degrees and then returned to its original position, the lumen 38 remains open to fluid flow.

Figure 5:
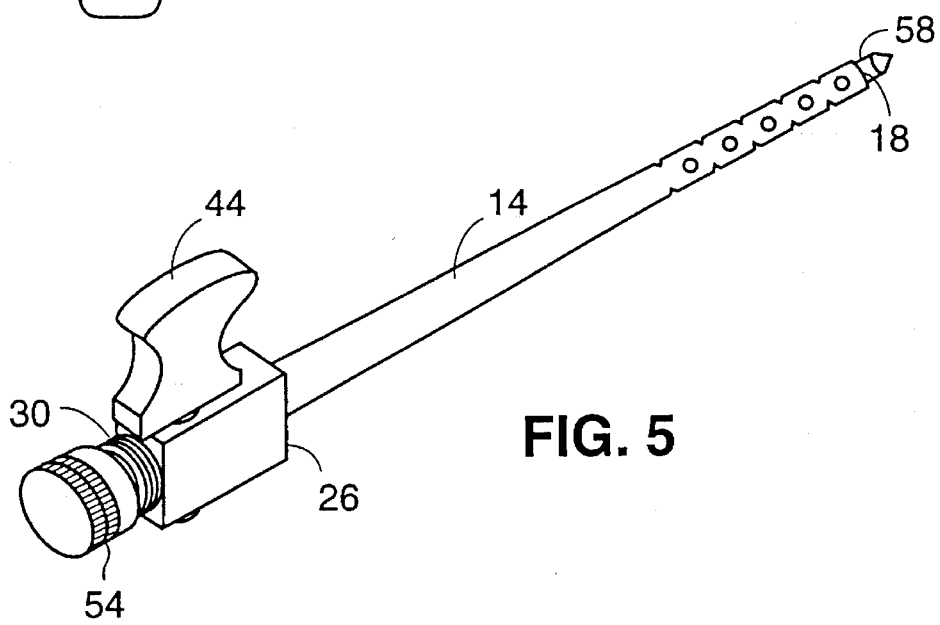
FIG. 5 is a perspective view of the cannula shown in FIG. 1 with a valve and trocar in place.

FIG. 5 illustrates the cannula 10 with the valve 44 positioned in the valve housing 26. The valve 44 is an "on-off" valve that allows liquids or other materials to pass through the section of the lumen 38 contained in the valve housing 26, when it is in the "on" position, and that blocks such passage when it is in the "off" position.

In FIG. 5, a trocar 54 is shown inserted in the lumen 38 of the cannula 10. A pointed tip 58 of the trocar 54 extends from the distal end 18 of the cannula 10 while the other end of the trocar 54 is screwed over the attachment means 30, thereby firmly securing the trocar 54 inside the cannula 10.

Figure 6:
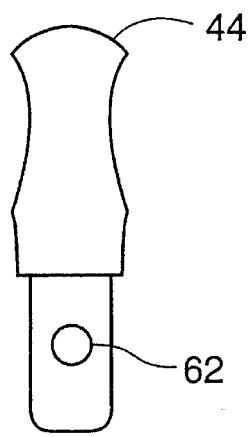
FIG. 6 is a front view of a valve for use in the cannula shown in FIG. 1.

FIG. 6 illustrates that the valve 44 includes an aperture 62 that allows liquid to flow through the valve 46 when the valve 44 is oriented in the "on" position, thereby connecting the lumens 38 and 39. When the valve 46 is rotated out of the "on" position, liquid can no longer pass through the aperture 62, thereby preventing liquid from flowing between the lumens 38 and 39.

Referring to FIGS. 1–5, the functioning of the inflow/outflow cannula 10 can now be explained. The cannula 10 is used during arthroscopic knee surgery to direct liquid such as saline or other sterile solutions, to or from the suprapatellar pouch (i.e. to introduce liquid into or to remove liquid from the suprapatellar pouch). As discussed previously, rigid cannulae of the prior art suffer from the problem of becoming blocked when the knee is bent during surgery and from the problem of occasionally causing bruising or perforation of tissue during the surgery.

The cannula 10 of the present invention avoids these problems because of the flexibility of the stem 14. During arthroscopic knee surgery, the cannula 10 is inserted into the suprapatellar pouch with the trocar 54 secured inside the cannula 10. The trocar is then removed from the cannula 10 and the valve 44 is closed. If the cannula 10 is to be used as an inflow cannula, fluid reservoir supply lines are attached between the attachment means 30 and an elevated supply of a liquid (such as saline), the valve 44 is opened and the liquid flows through the lumen 38 and out of the cannula 10 through the distal end 18 and apertures 34 into the suprapatellar pouch.

If the cannula 10 is to be used as an outflow cannula, a drainage tube is attached to the attachment means 30 instead of the fluid supply lines. Liquid is introduced into the suprapatellar pouch through the arthroscope enters the cannula 10 through the distal end 18 and apertures 34. When the valve 44 is opened, liquid flows through the apertures 38 and 39 and out of the proximal end 22 to the drainage tube.

The present inventor prefers using the cannula 10 in the "outflow" mode, but ultimately, the surgeon performing the arthroscopy will decide whether to use the cannula 10 as an inflow cannula or an outflow cannula.

During the arthroscopic procedure, when it becomes necessary to bend the knee, the cannula 10 is positioned in the suprapatellar pouch so that it will follow the curvature of the femoral condyles when the knee is bent. The rigidity of the stem 14 provided by the rigid segment 50, is sufficient to allow the cannula 10 to be repositioned without the need of reinserting the trocar 54.

When the knee is bent during the surgical procedure, the flexible segment 46 has sufficient flexibility to bend with the knee inside the compressed suprapatellar pouch. Because the stem 14 bends with knee, the flow of liquid into or out of the distal end 18 is not blocked. Additionally, since the stem 14 is flexible, there is much less likelihood that it will bruise or puncture tissue when the knee is bent.

It should be appreciated that although the preferred usage of the catheter 10 is in arthroscopic knee surgery, it is also useful in other types of arthroscopic surgery of joints, such as shoulder or elbow surgery.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

I claim:

1. A method for directing a liquid to or from a site during arthroscopic knee surgery comprising the steps of:

a) inserting a cannula/trocar assembly into the suprapatellar pouch of a human knee, the cannula comprising an elongated hollow stem having a flexible segment that includes a distal end of the cannula, and wherein the flexible segment is sufficiently flexible to bend through an angle of approximately ninety degrees and then return to an approximately straight position;

b) removing the trocar from the cannula; and c) allowing a liquid to flow through the cannula.

2. The method of claim 1 wherein a first outer diameter of the flexible segment, measured at a proximal end of the flexible segment, is greater than a second outer diameter of the flexible segment, measured at the distal end of the cannula.

3. The method of claim 1 wherein a first thickness of the flexible segment, measured at a proximal end of the flexible segment, is greater than a second thickness of the flexible segment, measured at the distal end of the cannula.

4. The method of claim 1 wherein the flexible segment is comprised of high density polyethylene.

* * * * *